(12) United States Patent
Pal et al.

(10) Patent No.: US 8,057,495 B2
(45) Date of Patent: Nov. 15, 2011

(54) ANEURYSM OCCLUSION DEVICE

(75) Inventors: Dharmendra Pal, Wilmington, MA (US); Roy S. Collins, Ellettsville, IN (US); Andrew W. Conder, Bloomington, IN (US); Kian Olsen, Bloomington, IN (US); Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1236 days.

(21) Appl. No.: 11/519,366

(22) Filed: Sep. 12, 2006

(65) Prior Publication Data
US 2007/0083257 A1     Apr. 12, 2007

Related U.S. Application Data

(60) Provisional application No. 60/716,698, filed on Sep. 13, 2005.

(51) Int. Cl.
*A61B 17/08* (2006.01)
(52) U.S. Cl. ...................................................... 606/157
(58) Field of Classification Search .................. 623/1.22; 606/200, 157, 113, 114, 127, 159
See application file for complete search history.

(56) References Cited

U.S. PATENT DOCUMENTS

| | | | |
|---|---|---|---|
| 5,250,071 A * | 10/1993 | Palermo | 606/198 |
| 5,417,708 A | 5/1995 | Hall et al. | |
| 5,649,949 A * | 7/1997 | Wallace et al. | 606/191 |
| 5,725,534 A | 3/1998 | Rasmussen | |
| 5,741,333 A | 4/1998 | Frid | |
| 5,849,037 A | 12/1998 | Frid | |
| 5,951,599 A | 9/1999 | McCrory | |
| 5,968,091 A | 10/1999 | Pinchuk et al. | |
| 6,010,498 A | 1/2000 | Guglielmi | |
| 6,051,021 A | 4/2000 | Frid | |
| 6,059,809 A | 5/2000 | Amor et al. | |
| 6,149,682 A | 11/2000 | Frid | |

(Continued)

FOREIGN PATENT DOCUMENTS
WO        WO 02/00139 A1     1/2002
(Continued)

OTHER PUBLICATIONS

International Search Report from corresponding PCT Application No. PCT/US2005/031277, dated Dec. 16, 2005, 4 pages.

*Primary Examiner* — Kevin T Truong
(74) *Attorney, Agent, or Firm* — Brinks Hofer Gilson & Lione

(57) ABSTRACT

A system and method for occluding an aneurysm formed in a dilatation area of a body vessel are disclosed. The system comprises a wire guide, a core wire, and an occlusion device. The wire guide comprises a proximal end and a distal end, and has a passageway that extends from the proximal end to the distal end. The core wire comprises a distal end and a proximal end, and is disposed through the passageway so that the proximal end of the core wire proximally extends beyond the proximal end of the wire guide. The occlusion device comprises a distal end and a proximal end, and has a deployed state and an undeployed state. The occlusion device has a pre-set spiraled coil shape when in the deployed state in the vessel. The occlusion device is disposed distally from the core wire in the passageway.

21 Claims, 6 Drawing Sheets

U.S. PATENT DOCUMENTS

| | | | |
|---|---|---|---|
| 6,152,144 A | 11/2000 | Lesh et al. | |
| 6,159,228 A | 12/2000 | Frid et al. | |
| 6,165,193 A | 12/2000 | Greene, Jr. et al. | |
| 6,168,592 B1 * | 1/2001 | Kupiecki et al. | 606/32 |
| 6,168,622 B1 | 1/2001 | Mazzocchi | |
| 6,237,460 B1 | 5/2001 | Frid | |
| 6,245,090 B1 | 6/2001 | Gilson et al. | |
| 6,379,329 B1 | 4/2002 | Naglreiter et al. | |
| 6,389,946 B1 | 5/2002 | Frid | |
| 6,497,671 B2 * | 12/2002 | Ferrera et al. | 600/585 |
| 6,500,190 B2 | 12/2002 | Greene, Jr. et al. | |
| 6,506,204 B2 | 1/2003 | Mazzocchi | |
| 6,508,833 B2 | 1/2003 | Pavcnik et al. | |
| 6,554,858 B2 | 4/2003 | Dereume et al. | |
| 6,569,190 B2 | 5/2003 | Whalen, II et al. | |
| 6,605,102 B1 | 8/2003 | Mazzocchi et al. | |
| 6,632,241 B1 | 10/2003 | Hancock et al. | |
| 6,666,892 B2 | 12/2003 | Hiles et al. | |
| 2001/0000797 A1 | 5/2001 | Mazzocchi | |
| 2002/0026234 A1 * | 2/2002 | Li et al. | 623/1.34 |
| 2002/0072689 A1 * | 6/2002 | Klint | 600/585 |
| 2002/0165572 A1 | 11/2002 | Saadat | |
| 2003/0013989 A1 | 1/2003 | Obermiller et al. | |
| 2003/0028209 A1 | 2/2003 | Teoh et al. | |
| 2003/0051735 A1 | 3/2003 | Pavcnik et al. | |
| 2003/0130689 A1 * | 7/2003 | Wallace et al. | 606/200 |
| 2004/0039435 A1 | 2/2004 | Hancock et al. | |
| 2004/0098102 A1 * | 5/2004 | Richter et al. | 623/1.15 |
| 2004/0166169 A1 | 8/2004 | Malaviya et al. | |
| 2004/0181186 A1 * | 9/2004 | Gellman et al. | 604/8 |
| 2004/0215332 A1 | 10/2004 | Frid | |
| 2004/0254625 A1 | 12/2004 | Stephens et al. | |
| 2004/0260384 A1 * | 12/2004 | Allen | 623/1.12 |

FOREIGN PATENT DOCUMENTS

| | | |
|---|---|---|
| WO | WO 02/47579 A1 | 6/2002 |
| WO | WO 02/071977 | 9/2002 |
| WO | WO 2005/117718 A1 | 12/2005 |

* cited by examiner

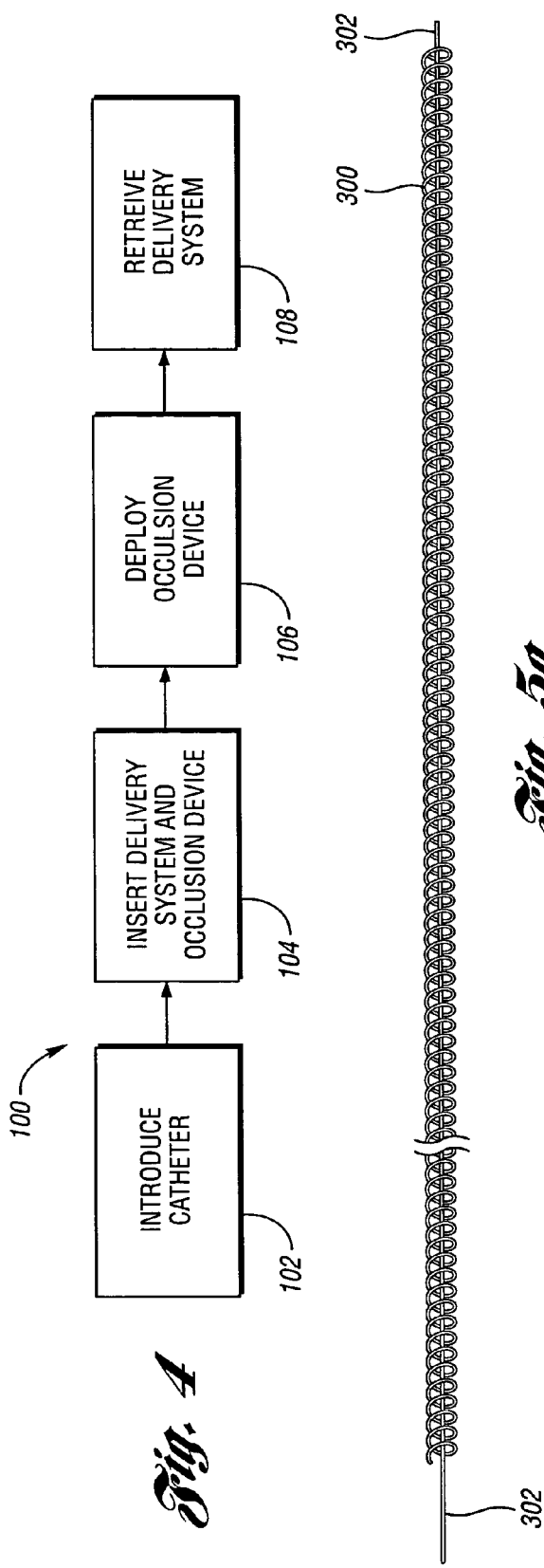
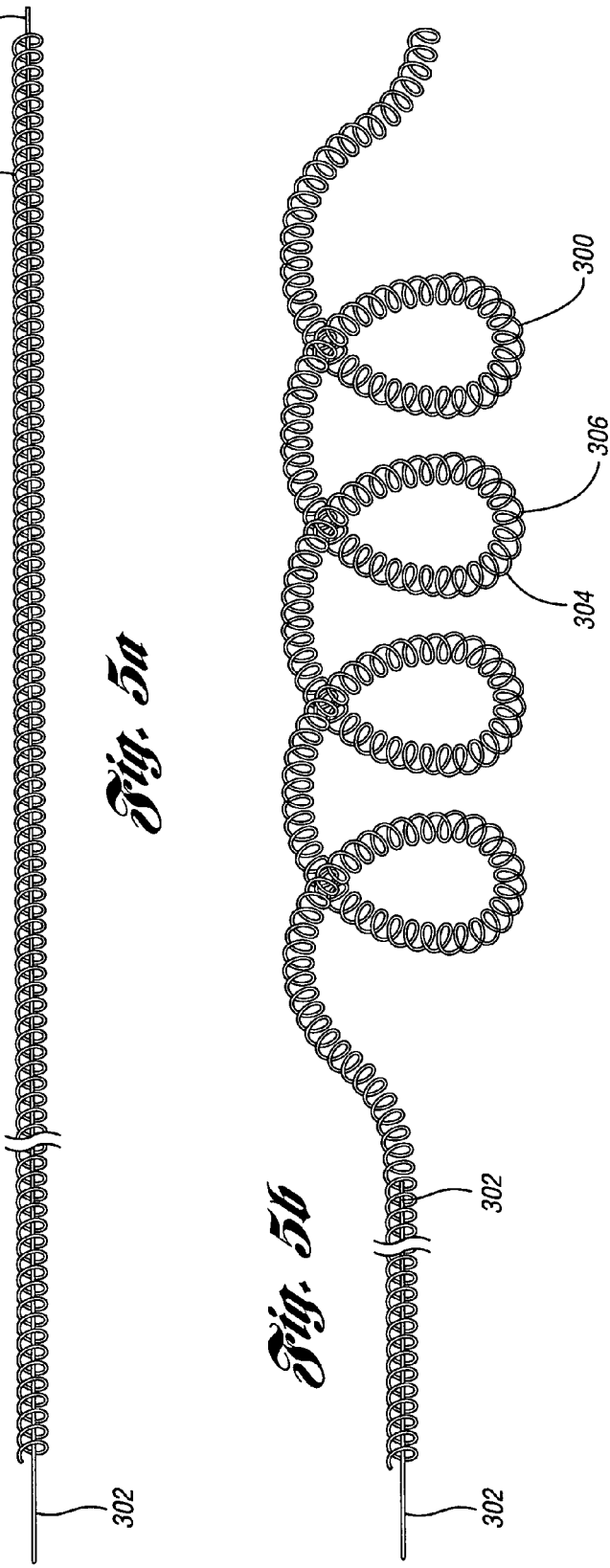
Fig. 4
Fig. 5a
Fig. 5b

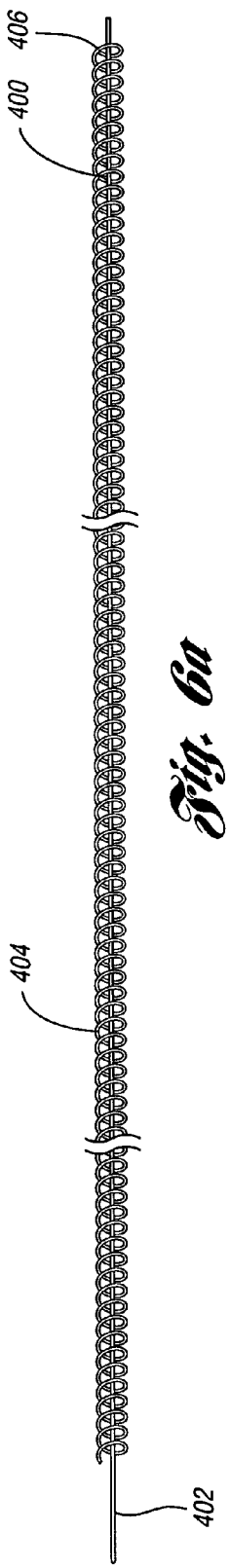
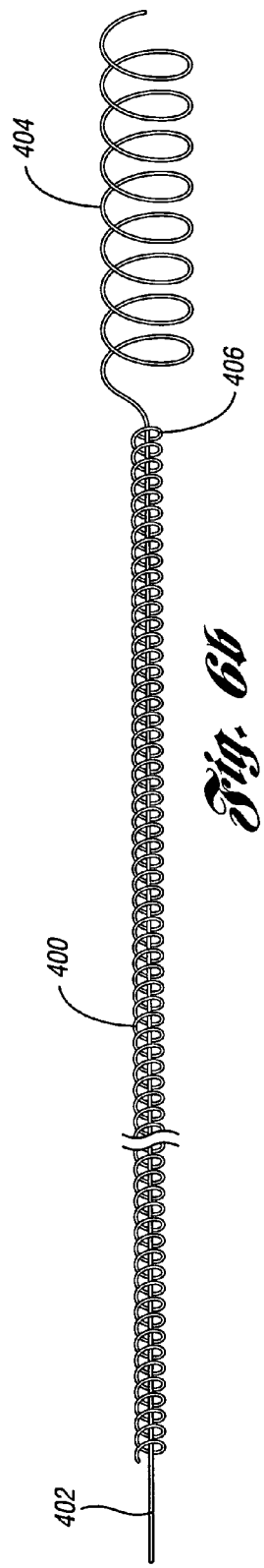
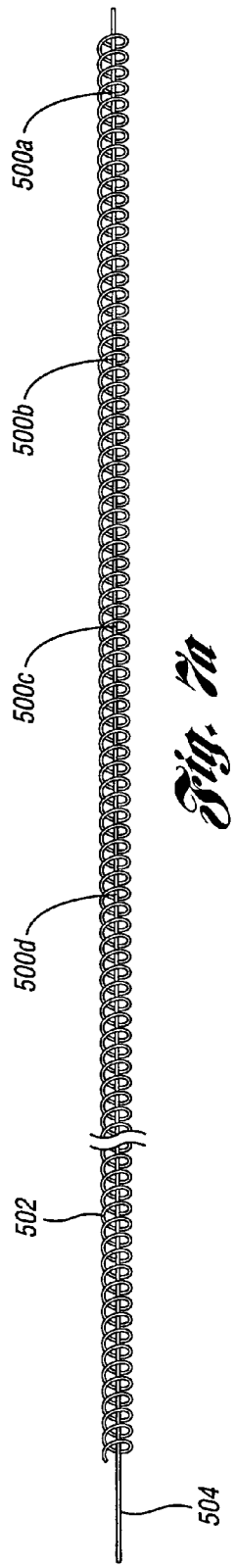
Fig. 6a
Fig. 6b
Fig. 7a

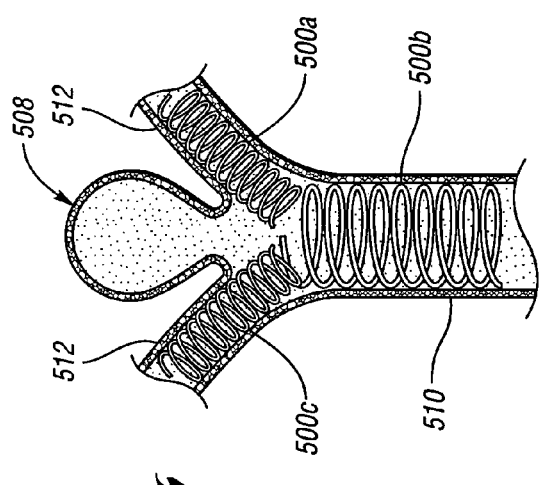
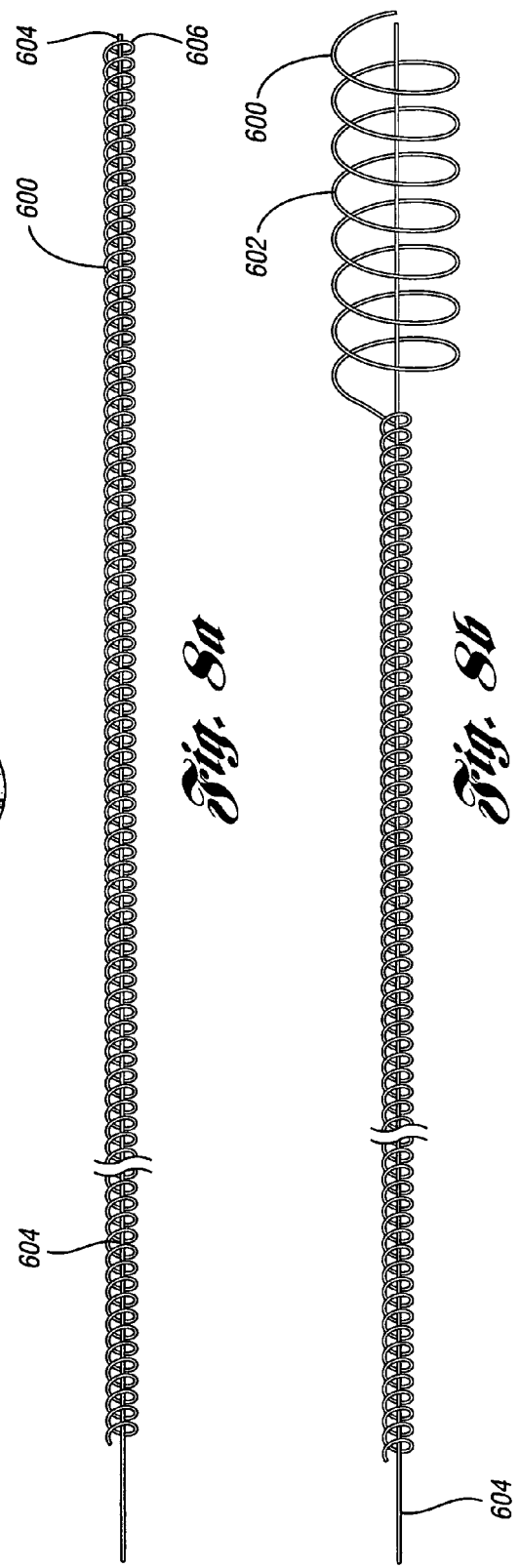

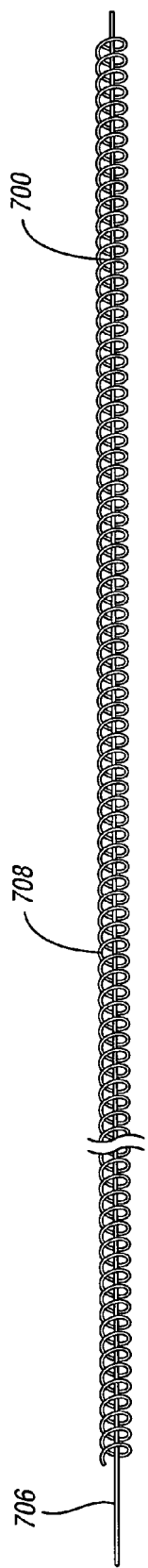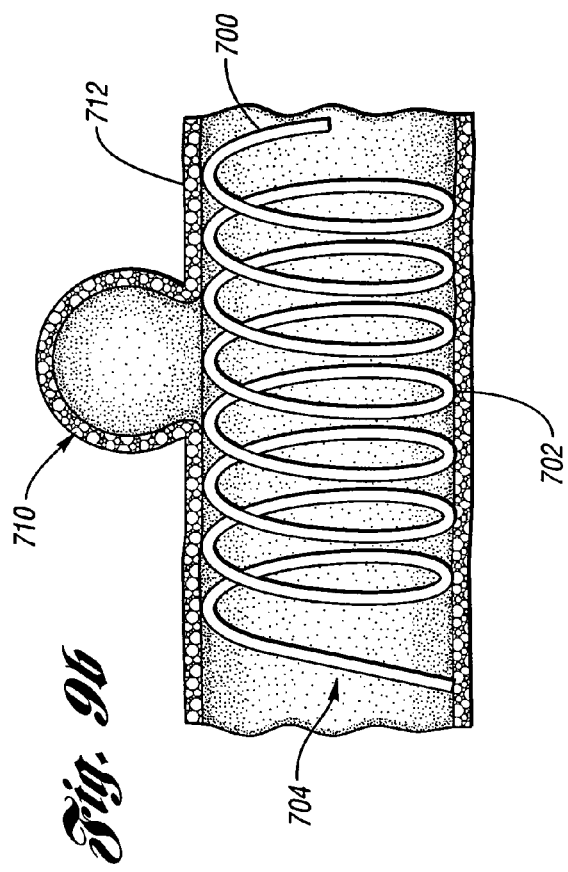
Fig. 9a
Fig. 9b

ANEURYSM OCCLUSION DEVICE

CROSS-REFERENCE TO RELATED APPLICATION

This application claims the benefit of U.S. Provisional Application No. 60/716,698, filed on Sep. 13, 2005, entitled "Aneurism Occlusion Device," the entire contents of which are incorporated herein by reference.

BACKGROUND OF THE INVENTION

The present invention relates to medical devices. More particularly, the invention relates to occluding devices and methods of occluding or sealing an aneurysm formed in a dilatation area of a body vessel.

Aneurysms, e.g., cerebral aneurysms, typically are formed as a result of the dilatation of a weakened wall of an artery, a vein, or the heart. Chief signs of an arterial aneurysm are the formation of a pulsating tumor, and often a bruit (aneurysmal bruit) heard over a swelling. Typically, aneurysms take on a dome shape to define a sac extending to a neck having an opening at a weakened or dilatation area of the body vessel.

Currently, there are a number of existing methods for the treatment of aneurysms. For example, one method involves an open surgical procedure in which, under microscopic dissection, a small vascular clip is placed across the neck of the aneurysm thereby excluding it from the circulation through the body vessel. However, treatment with surgery involves its inherent risks. Thus, many practitioners and patients prefer to avoid treatment with surgery when possible.

In another method, treatment involves an endovascular or "closed" approach in which a microcatheter is navigated from the femoral artery in the groin area into the cerebral vessels, allowing the placement of coils into the dome of the aneurysm. Under x-ray guidance, the coils are packed into the aneurysm, filling up its volume and thereby preventing blood from entering. This protects the patient from bleeding. However, many coils fail primarily due to continued growth of the aneurysm at the dilatation area of the body vessel proximal the neck of the aneurysm. Additionally, the insertion of coils into the dome of the aneurysm involves a substantial time consuming procedure with high costs.

Thus, there is a need to improve the current methods of treating aneurysms, for example cerebral aneurysms, without the relatively high risks, substantial time involved, and high costs.

BRIEF SUMMARY OF THE INVENTION

The present invention provides a system for an aneurysm. In general, the system includes a wire guide, a core wire, and an occlusion device for sealing or occluding an aneurysm formed in a dilatation area of a body vessel.

The wire guide comprises a proximal end and a distal end, and has a passageway that extends from the proximal end to the distal end. The core wire comprises a distal end and a proximal end, and is disposed through the passageway so that the proximal end of the core wire proximally extends beyond the proximal end of the wire guide. The occlusion device comprises a distal end and a proximal end, and has a deployed state and an undeployed state. The occlusion device has a pre-set spiraled coil shape when in the deployed state in the vessel. The occlusion device is disposed distally from the core wire in the passageway. The core wire is configured to move the occlusion device for deployment over the aneurysm of the body vessel to interfere with blood flow in the aneurysm.

Movement of the core wire in the distal direction urges the occlusion device out of the distal end of the wire guide, so that the occlusion device forms into its deployed state to occlude the aneurysm formed in the dilatation area of the body vessel. The occlusion device may be coated with an anti-thrombogenic material, a cytogenic material, or a thrombogenic material to control cell growth or thrombus formation in the occlusion device.

Further objects, features, and advantages of the present invention will become apparent from consideration of the following description and the appended claims when taken in connection with the accompanying drawings.

BRIEF DESCRIPTION OF THE DRAWINGS

FIG. 3b is an exploded view of the assembly of FIG. 3a;

FIG. 4 is a flow chart of a sequence of steps for deploying an occlusion device in accordance with an embodiment of the invention;

FIGS. 5a and 5b are perspective views of alternative occlusion device in accordance with the invention;

FIGS. 6a and 6b are perspective views of yet another alternative occlusion device in accordance with the invention;

FIGS. 7a and 7b are perspective views of yet another alternative occlusion device in accordance with the invention;

FIGS. 8a and 8b are perspective views of yet another alternative occlusion device in accordance with the invention; and FIGS. 9a and 9b are perspective and environment views of yet another alternative occlusion device in accordance with the invention.

DETAILED DESCRIPTION OF THE INVENTION

Figure 1:
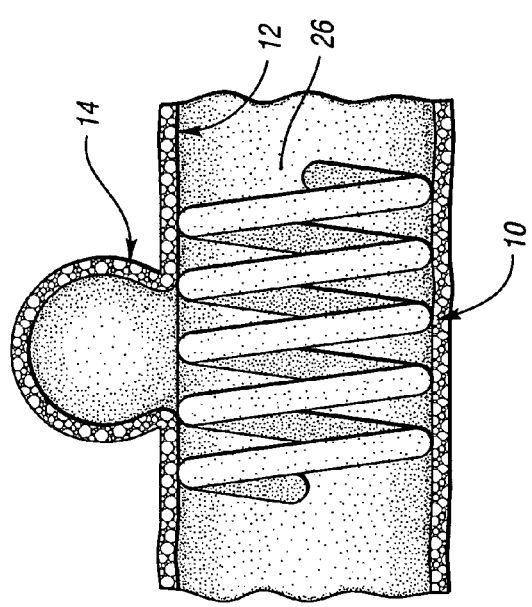
FIG. 1 is an environment view of an occlusion device in accordance with an embodiment of the present invention.
Figure 2:
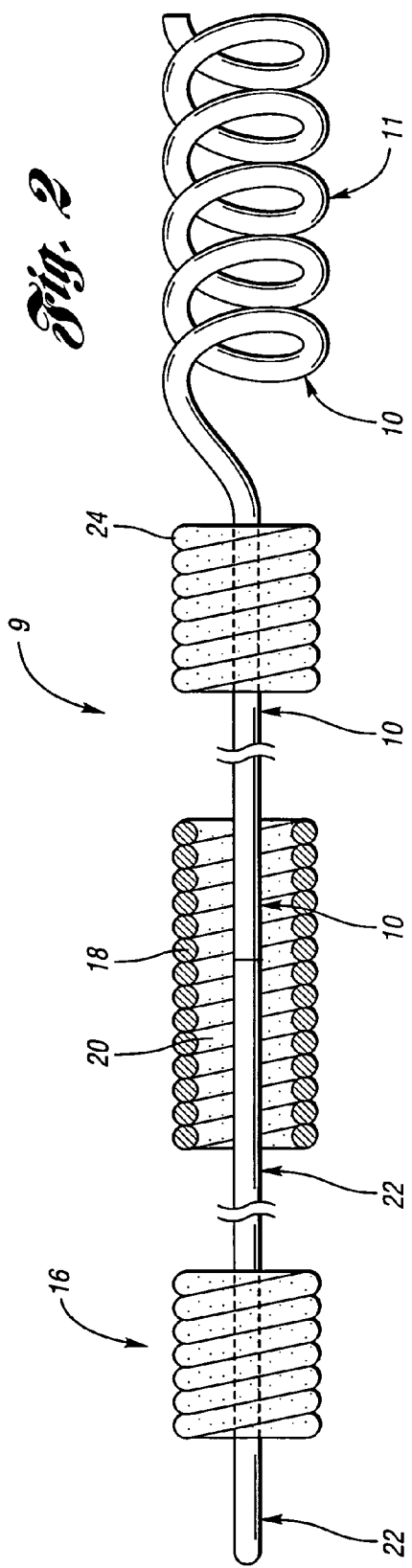
FIG. 2 is a perspective view of the occlusion device and associated delivery system in accordance with an embodiment of the present invention.

Referring now to FIGS. 1 and 2, a system 9 for occluding an aneurysm includes an occlusion device embodying the principles of the present invention that is illustrated therein and designated at 10. Embodiments of this invention involve the occlusion device 10 deployed within a vessel 12 to occlude an aneurysm formed in a dilatation area of the vessel, such as an artery, to occlude and stabilize an aneurysm 14, and hence to prevent rupture of the aneurysm. The aneurysm may be a neuro-aneurysm or any other type of aneurysm.

The system 9 also includes a delivery device 16, which is employed to implant the occlusion device 10 in the vessel 12 at the dilatation area forming the aneurysm. The delivery device 16 includes a coiled wire guide 18 with a passageway or channel 20 and a core wire 22 that reciprocates in the channel 20. Before the occlusion device 10 is placed at the aneurysm site, the device 10 is positioned within the channel 20 as an elongated wire such that the proximal end of the device 10 is in contact with the distal end of the core wire 22. After the distal end 24 of the wire guide 18 is positioned at the aneurysm site, a practitioner, such as a physician, pushes or advances the core wire 22 relative to the wire guide 18 to urge the occlusion device 10 to exit from the distal end 24. In this embodiment, the occlusion device is pre-set as a spiral or helical coil shape. Since the occlusion device 10 is pre-set as a helical coil, the occlusion device 10 takes the form of a spiraled coil with multiple coils 13 in the vessel 12 as the device exits the wire guide 18 to cut off blood supply to the aneurysm 14.

In this embodiment, the occlusion device 10 may be coated with one of an anti-thrombogenic material, a cytogenic material or a thrombogenic material to control cell growth or thrombus formation 26 to block or seal the aneurysm 14 from the vessel 12. Such coatings may be used individually or in combination with each other. For example, the portion of the occlusion device intended to interfere with blood flow to the aneurysm may be coated with thrombogenic material. The remainder of the occlusion device may be coated with anti-thrombogenic material so as to prevent the formation of thrombus that could occlude blood flow through the body vessel.

In a particular implementation, the core wire 22 has a length of between about 80 and 300 centimeters (cm) and a diameter of about 0.001 to 0.035 inch (in). In a certain implementation, the length of the core wire 22 is about 180 cm and the diameter of the core wire is about 0.006 in.

The wire guide 18 may have a length in the range between about 80 to 300 cm, a coil diameter in the range between about 0.006 to 0.036 in, and a wire diameter in the range between about 0.0005 to 0.005 in. Preferably, the length of the wire guide is about 180 cm, the coil diameter is about 0.014 in, and the wire diameter is about 0.001 in.

The occlusion device may have a length of about 1 cm and a diameter of about 4 millimeters (mm). The core wire 22 and the wire guide 18 may be made from the same material as the occlusion device 10.

The occlusion device 10 may be formed from any suitable material such as a superelastic material, stainless steel wire, cobalt-chromium-nickel-molybdenum-iron alloy, or cobalt-chrome alloy. It is understood that in some implementations the occlusion device 10 may be formed of any other suitable material that will result in a self-coiling device, such as shape memory alloys. Shape memory alloys have the desirable property of becoming rigid, that is, returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenite, such that the material returns to its remembered state. The transition temperature is dependent on the relative proportions of the alloying elements Ni and Ti and the optional inclusion of alloying additives.

In one embodiment, the occlusion device 10 is made from Nitinol with a transition temperature that is below normal body temperature of humans (i.e., below 98.6° F.). Thus, when the occlusion device 10 is deployed in a body vessel and exposed to normal body temperature, the alloy in the occlusion device 10 transforms to austenite, such that the device returns to its remembered state, which for the present invention is a coiled configuration.

As shown in FIG. 1, the occlusion device is configured to be deployed over the aneurysm of the body vessel. As shown, the coil of the occlusion device remains open to allow the passage of blood therethrough. Due to the interference of blood flow into the aneurysm dome, a clot will eventually form in the aneurysm, thereby relieving blood pressure from the weakened dome wall and preventing a rupture.

Figure 3A:
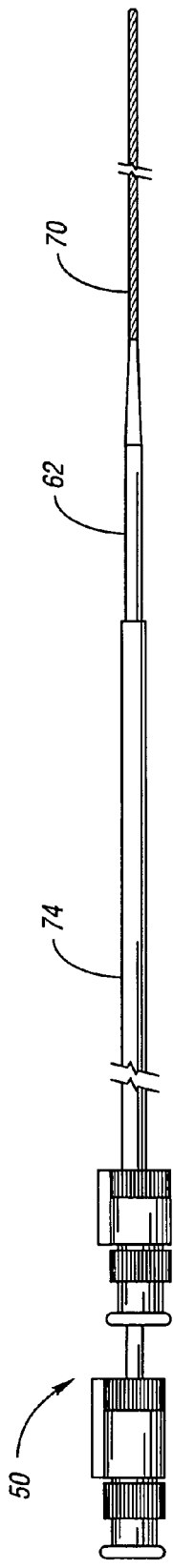
FIG. 3a is a side view of an occlusion protection assembly for occluding an aneurysm formed in a dilatation area of a body vessel.
Figure 3B:
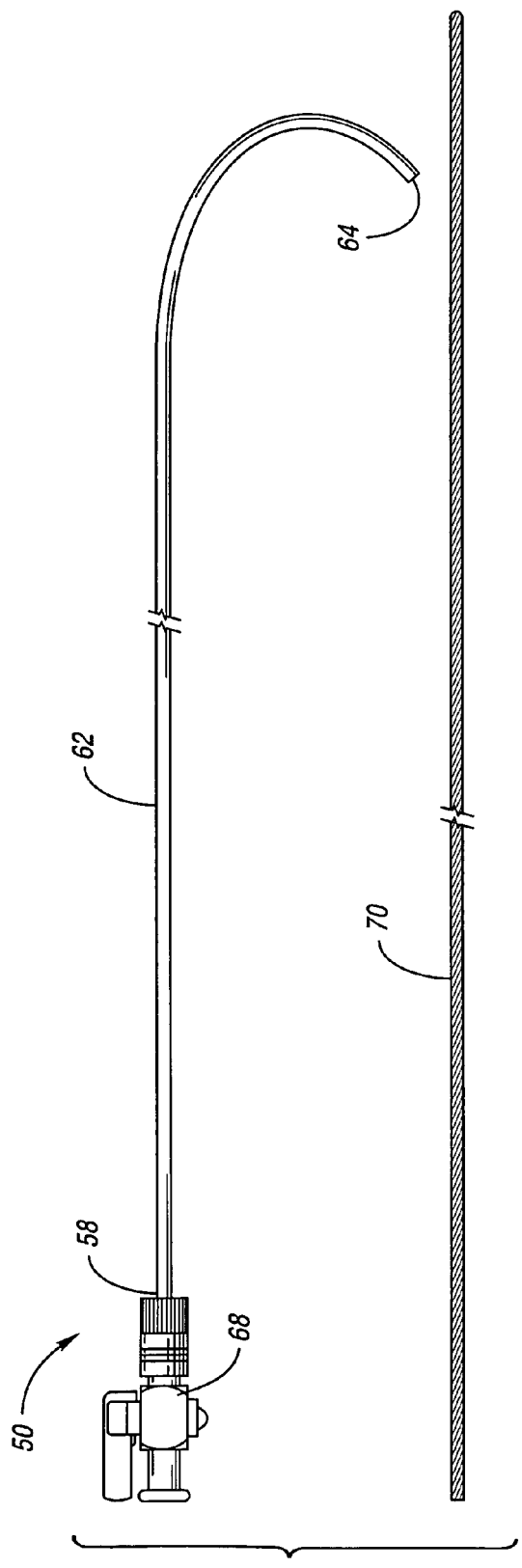

The occlusion device 10 may be used independently with the delivery system 16 without any other delivery system or mechanism. Alternatively, the device 10 and delivery device 16 may be used, for example, with an assembly 50 as depicted in FIGS. 3a and 3b.

As shown, the assembly 50 includes an inner catheter 62 with a distal end 64 through which the system 9 is positioned for deployment in the body vessel to occlude an aneurysm formed at a dilatation area of the vessel. The inner catheter 62 is preferably made of a soft, flexible material such as Teflon™ or polytetrafluoroethylene (PTFE), or any other suitable material. Generally, the inner catheter 62 also has a proximal end 58 and a plastic adaptor or hub 68 to receive the system 9. The size of the inner catheter 62 is based on the size of the body vessel into which the catheter 62 is inserted, and the size of the coiled wire guide 18.

The assembly 50 may also include a wire guide 70 configured to be percutaneously inserted within the vasculature to guide the inner catheter 62 to a location adjacent an aneurysm. Alternatively, the system 9 may be employed as a wire guide.

In use, the system 9 is placed in the inner catheter 62 prior to treatment of the aneurysm. The system 9 is then guided through the inner catheter preferably from the hub 72 and distally beyond the distal end 64 of the inner catheter 62 to a location within the vasculature near the aneurysm.

The assembly 50 may include a polytetrafluoroethylene (PTFE) introducer sheath 74 for percutaneously introducing the wire guide 70, or the system 9, and the inner catheter 62 in a body vessel. Of course, any other suitable material may be used for the sheath 74. The introducer sheath 74 may have any suitable size, e.g., between about three-french and eight-french. The introducer sheath 74 facilitates inserting the inner catheter 62 percutaneously to a desired location in the body vessel and provides stability to the inner catheter at a desired location in the body vessel. For example, as the introducer sheath 74 is held stationary within an artery, it adds stability to the inner catheter 62, as the inner catheter 62 is advanced through the introducer sheath 74 to a desired location in the vasculature.

When the distal end 64 of the inner catheter 62 is at a location near the aneurysm, the system 9 is inserted through the inner catheter 62 and is advanced coaxially through the inner catheter 62 for deployment through the distal end 64 of the inner catheter. In this configuration, the proximal end of the wire guide 18 can be used to mechanically advance or push the system 9 through the catheter.

FIG. 4 depicts a sequence of steps of a process 100 for occluding an aneurysm when employing the assembly 50. In step 102, the medical practitioner, such as a physician, introduces the inner catheter 62 in a body vessel. The physician may use any suitable means, for example, fluoroscopy, to verify the placement of the inner catheter near the location of the aneurysm.

Next, in step 104, the delivery device 16 and the occlusion device 10 are placed in the inner catheter 62 and advanced beyond the distal end of the inner catheter. In step 106, the physician pushes on the core wire 22 to advance the occlusion device 10 out of the distal end 24 of the wire guide 18. After the occlusion device 10 is deployed, in step 108, the physician retrieves the delivery device 16 from the catheter 62. The physician may also retrieve the catheter 62. Optionally, the catheter 62 may remain in place for use with some alternative treatment device.

It is to be noted that the wire guide may be a relatively small diameter catheter tube. In this example, the wire guide is made of Teflon™ or polytetrafluoroethylene (PTFE) and has an inside diameter that is configured to accept the coil in its straight, undeployed state. The outside diameter of the wire guide is sized to fit the inside of the inner catheter mentioned above or another guide catheter. In one example, the outside diameter of the wire guide is preferably between about 2 and 5 french and the inside diameter may be between about 0.005 and 0.060 inch, and more preferably between about 3 and 4 french (between about 0.035 and 0.055 inch) and the inside diameter may be between about 0.010 and 0.040 inch.

Other embodiments are within the scope of the invention. For example, referring to FIGS. 5a and 5b, there is shown an occlusion device 300 initially shaped (FIG. 5a) as a coiled wire guide. As the physician pulls a core wire 302 out from the interior of the occlusion device 10, the device 10 takes its pre-shape configuration shown in FIG. 5b. When deployed, the occlusion device 300 is configured as a spiraled or helical coil with a plurality of primary coils 304 and secondary coils 306.

An alternative occlusion device 400 is shown in FIGS. 6a and 6b. Initially, the occlusion device 400 in its undeployed state is a straight wire positioned within a coiled wire guide 404. To deploy the occlusion device 400, the practitioner pushes a core wire 402 through the wire guide 404 such that the occlusion device 400 exits the distal end 406 of the wire guide 404, which is configured to form the occlusion device 400 into a spiraled coil as shown in FIG. 6b.

In some situations, it may be desirable to deploy multiple occlusion devices from a single delivery system. For example, as shown in FIGS. 7a and 7b, multiple occlusion devices 500a, 500b, 500c, and 500d initially reside in a coiled wire guide 502. As the practitioner pushes on a core wire 504 through the wire guide 502, the occlusion devices exit the wire guide 502 to occlude, for example, a main branch 510 and secondary branches 512 of a vasculature shown in FIG. 7b to cut off blood supply to an aneurysm 508.

In another embodiment, as shown in FIGS. 8a and 8b, a coiled occlusion device 600 is initially positioned about a core wire 604 in the form of a wire guide. The distal end 606 of the occlusion device is also initially engaged with the core wire 604. To deploy the occlusion device 600 in a body vessel, the practitioner pushes or pulls on the core wire 604 to disengage the distal end 606 of the occlusion device from the core wire. Once this occurs, the occlusion device 600 expands to a pre-set shape as a spiraled coil with multiple coils 602 to interfere with blood flow to an aneurysm formed in a dilatation area of a body vessel.

In yet another embodiment, an occlusion device 700, in its undeployed state, initially resides in a wire guide 708. The occlusion device 700 is deployed in a manner similar to that performed to deploy the occlusion device 10 described above. Specifically, a practitioner pushes a core wire 706 through the wire guide 708 to urge the occlusion device 700 to exit from the distal end of the wire guide 708. Since the occlusion device 700 is pre-set as a helical coil, the occlusion device 700 takes the form of a spiraled coil with multiple coils in the vessel 712 as the device exits the wire guide 708 to cut off blood supply to the aneurysm 710. Once deployed, the occlusion device 700 has an additional feature, namely, a straight segment 704, which acts as a leaf spring by applying a force to the interior surface of the vessel 712, thereby anchoring the occlusion device 700 in the vessel 712.

Any of the occlusion devices described with reference to FIGS. 5 through 9 may be coated with one of an anti-thrombogenic material, a cytogenic material, or a thrombogenic material to expedite cell growth or thrombus formation to block or seal the aneurysm from the vessel. Further, any of these occlusion devices may be used in combination with the assembly 50 shown in FIG. 3.

While the present invention has been described in terms of preferred embodiments, it will be understood, of course, that the invention is not limited thereto since modifications may be made to those skilled in the art, particularly in light of the foregoing teachings.

What is claimed is:

1. A system for occluding an aneurysm formed in a dilatation area of a body vessel, the system comprising:
   a wire guide with a proximal end and a distal end, the wire guide having a passageway that extends from the proximal end to the distal end;
   a core wire with a distal end and a proximal end, the core wire being disposed through the passageway so that the proximal end of the core wire proximally extends beyond the proximal end of the wire guide; and
   a plurality of occlusion devices in contact together and disposed in series in the passageway of the wire guide and having a distal end and a proximal end, the occlusion devices having a deployed state and an undeployed state, the occlusion devices having a pre-set spiraled coil shape and having different outside diameters when in the deployed state in the vessel, the occlusion devices being disposed distally from the core wire in the passageway, the core wire being configured to move the occlusion devices for deployment over the aneurysm of the body vessel to interfere with blood flow in the aneurysm.

2. The system of claim 1 wherein the wire guide is a coiled wire.

3. The system of claim 1 wherein the distal end of the wire guide is configured to form the occlusion devices into a spiraled coil shape.

4. The system of claim 1 wherein the occlusion devices are disposed in the passageway of the wire guide and movement of the core wire in the distal direction urges the occlusion devices out of the distal end of the wire guide to deploy the occlusion devices.

5. The system of claim 1 wherein the wire guide is made of superelastic material.

6. The system of claim 1 wherein the core wire is made of superelastic material.

7. The system of claim 1 wherein the occlusion devices are incorporated into the wire guide, the occlusion devices expanding about the core wire when expanding to the deployed state, at least one of the occlusion devices having primary coils and secondary coils when in the deployed state.

8. The system of claim 1 wherein the occlusion devices are coated with at least one of a cytogenic material, a thrombogenic material, and an anti-thrombogenic material.

9. The system of claim 1 wherein the occlusion devices are incorporated into the wire guide, the distal end of the occlusion devices being engaged to the core wire prior to deployment of the occlusion devices, movement of the wire guide relative to the occlusion devices disengaging the distal end of the occlusion devices from the core wire resulting in the occlusion devices expanding about the core wire.

10. The system of claim 1 wherein the occlusion devices are formed from a wire.

11. The system of claim 10 wherein the occlusion devices each include a straight segment which acts as a leaf spring by applying a force to the interior surface of the vessel to anchor the occlusion devices in the vessel.

12. The system of claim 10 wherein the wire is made of superelastic material.

13. The system of claim 12 wherein the superelastic material is Nitinol.

14. The system of claim 1 wherein at least one of the occlusion devices have a diameter of about 4 millimeters when in the deployed state.

15. The system of claim 1 further wherein the plurality of occlusion devices are deployed in different branches of the body vessel.

16. A method for occluding an aneurysm formed in a dilatation area of a body vessel, the method comprising:
   disposing a wire guide in the vessel, the wire guide having distal end and a proximal end, the wire guide having a passageway that extends between the distal and proximal ends; and
   moving a plurality of occlusion devices in contact together and that are arranged in series in the passageway of the wire guide with a core wire through the passageway to deploy the occlusion devices in the body vessel over the aneurysm, the occlusion devices having a spiraled coil shape and having different outside diameters when deployed in the vessel.

17. The method of claim 16 wherein the wire guide is a coiled wire.

18. The method of claim 16 the occlusion devices are coated with at least one of a cytogenic material, a thrombogenic material, and an anti-thrombogenic material.

19. The method of claim 16 wherein the occlusion devices are formed from a wire.

20. The method of claim 19 wherein the wire is made of superelastic material.

21. The method of claim 20 wherein the superelastic material is Nitinol.

* * * * *